United States Patent [19]

Mosher et al.

[11] Patent Number: 5,460,955
[45] Date of Patent: * Oct. 24, 1995

[54] FIBRONECTIN PURIFICATION VECTOR

[75] Inventors: Deane F. Mosher; Jane M. Sottile, both of Madison, Wis.

[73] Assignee: Wisconsin Alumni Research Foundation, Madison, Wis.

[ * ] Notice: The portion of the term of this patent subsequent to Aug. 30, 2011 has been disclaimed.

[21] Appl. No.: 145,061

[22] Filed: Oct. 28, 1993

Related U.S. Application Data

[63] Continuation-in-part of Ser. No. 637,250, Jan. 3, 1991, Pat. No. 5,342,762.

[51] Int. Cl.$^6$ .............................. C07K 1/22; C07K 1/14; C12N 15/09; C12N 15/63
[52] U.S. Cl. .................. 435/69.7; 435/69.1; 435/172.3; 530/412; 530/413
[58] Field of Search .................. 435/69.1, 69.7, 435/69.8, 172.3, 320.1, 240.2, 272, 273; 530/412, 415, 413; 536/24.1, 23.4; 935/24, 48

[56] References Cited

U.S. PATENT DOCUMENTS 5,342,762  8/1994  Mosher .................................. 435/69.1

OTHER PUBLICATIONS

F. Blumenstock, et al., 132 Meth. Enzym. 334–349 (1986).
E. Barry, et al., 263 J. Bio. Chem. 10464–10469 (1988).
J. Vaughn, et al., 13 In Vitro 213–217 (1977).
D. Miller, et al., 8 Genetic Engineering: Principals & Methods 277–298 (1986).
Y. Matsuura, et al., 67 J. Gen. Virol. 1515–1529 (1986).
M. Summers, et al., Tex. Agri. Exp. Stn. Bull. 5–56 (1987).
K. Mullis, et al., 155 Meth. Enzyn. 335–350 (1987).
R. Patel, et al., 6 Embo. Journal 2565–2572 (1987).
L. Miller, et al., 42 Ann. Rev. Microbiol. 177–99 (1988).
T. Kunkel, et al., *Recombinant DNA Methodology* 587–601 (1989).
T. Petersen, et al., 80 PNAS UA 137–141 (1983).
E. Ruoslahti, 57 Ann. Rev. Biochem. 375–413 (1988).
T. Petersen, et al., in *Fibronectin* 1–24 (1989).
K. Yamada, et al., in *Fibronectin* 47–121 (1989).
J. Thiery, et al., in *Fibronectin* 181–213 (1989).
R. Covin, in *Fibronectin* 213–254 (1989).
P. 204 of a Promega catalog showing the pGEM–4 vector.
P. 220 of a Promega catalog showing the pGEM–72f(=) art.
J. Sambrook, et al. Molecular Cloning, A Laboratory Manual, Cold Spring Harbor, 16.45–16.46 (1989).
Astermark, et al., "Baculovirus–mediated Expression of the Epidermal Growth Factor–like Modules of Human Factor IX Fused to the Factor XIIIa Transamidation Site in Fibronectin," *The Journal of Biological Chemistry,* 269:3690–3697, 1994.
Sottile, et al., "Assembly of Fibronectin Molecules with Mutations or Deletions of the Carboxyl–Terminal Type I Modules," *Biochemistry,* 32:1641–1647, 1993.
Mosher, et al., *Fibronectin,* pp. 68–72, 1988.
Mosher, et al., "Cross–linking of Collagen and Fibronectin by Factor XIIIa," *The Journal of Biological Chemistry,* 255:1181–1188, 1980.

*Primary Examiner*—Robert A. Wax
*Assistant Examiner*—Dian C. Jacobson
*Attorney, Agent, or Firm*—Quarles & Brady

[57] ABSTRACT

Recombinant protein purification vectors and methods for their use are disclosed. The vectors contain a DNA sequence coding for a gelatin binding region of fibronectin. The vectors express a foreign DNA sequence of interest fused to the fibronectin portion. Secretion signals on the fused product assist the product in being secreted from a production cell. The product can then be purified on a gelatin-containing affinity column and digested with a protease, such as trypsin, to cleave the desired protein from the gelatin binding region. The protein then contains no more than one extraneous amino acid.

5 Claims, 2 Drawing Sheets

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 39 bases
        ( B ) TYPE: nucleic acid
        ( C ) STRANDEDNESS: single
        ( D ) TOPOLOGY: linear ( i i ) MOLECULE TYPE: Other Nucleic Acid ( i i i ) HYPOTHETICAL: YES ( i v ) ANTI-SENSE: NO ( x i ) SEQUENCE DESCRIPTION: SEQ ID NO:1:

```
TGGCTGTCAG  TCAGAGCAAG  GAGAAATGTT  TTGATCACG                        39
```

( 2 ) INFORMATION FOR SEQ ID NO:2:

( i ) SEQUENCE CHARACTERISTICS:
        ( A ) LENGTH: 41 bases
        ( B ) TYPE: nucleic acid
        ( C ) STRANDEDNESS: single
        ( D ) TOPOLOGY: linear ( i i ) MOLECULE TYPE: Other Nucleic Acid ( i i i ) HYPOTHETICAL: YES ( i v ) ANTI-SENSE: NO ( x i ) SEQUENCE DESCRIPTION: SEQ ID NO:2:

```
GGTGGCTGTC  AGTCAGAGCA  AGGTTCTACA  GAGTCTTCAG  C                    41
```

( 2 ) INFORMATION FOR SEQ ID NO:3:

( i ) SEQUENCE CHARACTERISTICS:
        ( A ) LENGTH: 34 bases
        ( B ) TYPE: nucleic acid
        ( C ) STRANDEDNESS: single
        ( D ) TOPOLOGY: linear ( i i ) MOLECULE TYPE: Other Nucleic Acid ( i i i ) HYPOTHETICAL: YES ( i v ) ANTI-SENSE: NO ( x i ) SEQUENCE DESCRIPTION: SEQ ID NO:3:

CGTGCAGCCT CCATCCCCGT GGGCTGTCAG TCAG     34

(2) INFORMATION FOR SEQ ID NO:4:

(i) SEQUENCE CHARACTERISTICS:
        (A) LENGTH: 12 bases
        (B) TYPE: nucleic acid
        (C) STRANDEDNESS: single
        (D) TOPOLOGY: linear (ii) MOLECULE TYPE: Other Nucleic Acid (iii) HYPOTHETICAL: YES (iv) ANTI-SENSE: NO (xi) SEQUENCE DESCRIPTION: SEQ ID NO:4:

CCANNNNNT GG     12

(2) INFORMATION FOR SEQ ID NO:5:

(i) SEQUENCE CHARACTERISTICS:
        (A) LENGTH: 32 bases
        (B) TYPE: nucleic acid
        (C) STRANDEDNESS: single
        (D) TOPOLOGY: linear (ii) MOLECULE TYPE: Other Nucleic Acid (iii) HYPOTHETICAL: YES (iv) ANTI-SENSE: NO (xi) SEQUENCE DESCRIPTION: SEQ ID NO:5:

GGCCACGGGG ATGGGCCAGT GGTACCATCG GG     32

(2) INFORMATION FOR SEQ ID NO:6:

(i) SEQUENCE CHARACTERISTICS:
        (A) LENGTH: 32 bases
        (B) TYPE: nucleic acid
        (C) STRANDEDNESS: single
        (D) TOPOLOGY: linear (ii) MOLECULE TYPE: Other Nucleic Acid (iii) HYPOTHETICAL: YES (iv) ANTI-SENSE: NO (xi) SEQUENCE DESCRIPTION: SEQ ID NO:6:

GGCCATCCCC GTGGGCAACG TGTTATGACG AC     32

(2) INFORMATION FOR SEQ ID NO:7:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: N-terminal (ix) FEATURE:
        (A) NAME/KEY: Modified-site
        (B) LOCATION: 1..2

(D) OTHER INFORMATION: /label=Modification
/ note="The first residue is
pyroglutamic acid."

(ix) FEATURE:
(A) NAME/KEY: Modified-site
(B) LOCATION: 13..18
(D) OTHER INFORMATION: /label=insertion /note="The
sequence Xaa Xaa Xaa Xaa Xaa
Xaa indicates the position of
the inserted foreign amino
acid."

(xi) SEQUENCE DESCRIPTION: SEQ ID NO:7:

| Xaa | Ala | Gln | Gln | Ile | Val | Gln | Pro | Pro | Ser | Pro | Trp | Xaa | Xaa | Xaa | Xaa |
| 1 | | | | 5 | | | | | 10 | | | | | 15 | |

| Xaa | Xaa | Pro | Ser | Pro | Trp | Ala | Val | Ser | Gln | Ser | Lys | Val | Leu | Gln | Ser |
| | | | 20 | | | | | 25 | | | | | 30 | | |

| Ala | Ser | Ala | Gly | Ser | Gly | Ser | Phe | Thr | Asp | Val | Arg |
| | | 35 | | | | | 40 | | | | |

(2) INFORMATION FOR SEQ ID NO:8:

(i) SEQUENCE CHARACTERISTICS:
(A) LENGTH: 986 base pairs
(B) TYPE: nucleic acid
(C) STRANDEDNESS: double
(D) TOPOLOGY: linear (ii) MOLECULE TYPE: cDNA (iii) HYPOTHETICAL: NO (vi) ORIGINAL SOURCE:
(A) ORGANISM: Rattus norvegicus (xi) SEQUENCE DESCRIPTION: SEQ ID NO:8:

```
GTTCTACAGA GTGCTTCAGC TGGATCTGGC TCCTTCACAG ATGTCCGAAC AGCTATTTAC        60
CAACCCCAGA CCCACCCCCA GCCCGCACCG TACGGCCACT GTGTCACAGA CAGCGGTGTG       120
GTCTACTCTG TGGGAATGCA GTGGCTGAAG TCTCAAGGAG ACAAGCAGAT GCTGTGCACT       180
TGCCTGGGCA ATGGCGTCAG CTGCCAGGAG ACAGCTGTGA CCCAGACTTA CGGTGGCAAC       240
TCAAACGGGG AGCCCTGTGT TCTCCCGTTT CACTACAACG GTAGGACCTT CTACTCCTGC       300
ACCACCGAAG GGCGGCAAGA CGGACATCTG TGGTGTAGCA CAACTTCAAA TTATGAACAA       360
GACCAGAAGT ATTCTTTCTG CACAGACCAC GCGGTTTTGG TTCAGACTCG AGGTGGGAAT       420
TCCAATGGTG CCTTGTGCCA CTTCCCCTTC CTGTACAGCA ACCGGAATTA CAGCGACTGT       480
ACTTCTGAGG GTAGGCGGGA CAACATGAAA TGGTGCGGCA CCACCCAGAA CTACGATGCC       540
GATCAGAAGT TTGGATTCTG CCCAATGGCT GCCCATGAGG AGATCTGCAC GACCAACGAA       600
GGGGTCATGT ATCGCATTGG GGACCAGTGG GATAAGCAGC ATGACCTGGG CCACATGATG       660
AGGTGCACGT GTGTTGGGAA CGGCCGTGGA CAATGGGCCT GCATCCCTA CTCCCAGCTC       720
CGAGATCAGT GCATCGTTGA TGACATTACT TACAACGTCA ACGACACGTT CCACAAGCGT       780
CACGAGGAGG GACATATGCT GAACTGTACC TGCTTCGGTC AGGGCCGGGG CAGATGGAAA       840
TGTGACCCCA TCGACCGATG CCAAGATTCA GAGACCCGGA CATTTTACCA GATTGGTGAC       900
TCCTGGGAGA AGTTTGTGCA TGGTGTCAGA TACCAGTGTT ACTGTTACGG CCGTGGCATT       960
GGGGAGTGGC ACTGCCAGCC TCTGCA                                            986
```

(2) INFORMATION FOR SEQ ID NO:9:

(i) SEQUENCE CHARACTERISTICS:

(A) LENGTH: 12 base pairs
            (B) TYPE: nucleic acid
            (C) STRANDEDNESS: single
            (D) TOPOLOGY: linear (ii) MOLECULE TYPE: Other Nucleic Acid (xi) SEQUENCE DESCRIPTION: SEQ ID NO:9:

AAGACGCGTA GG                                                           12

(2) INFORMATION FOR SEQ ID NO:10:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: Peptide Fragment (xi) SEQUENCE DESCRIPTION: SEQ ID NO:10:

Lys Thr Arg Arg
    1

(2) INFORMATION FOR SEQ ID NO:11:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: Oligonucleotide (xi) SEQUENCE DESCRIPTION: SEQ ID NO:11:

GAAACCGGGA AGACGCGTAG GCAGGCTCAG C                                      31

(2) INFORMATION FOR SEQ ID NO:12:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: Other Nucleic Acid (xi) SEQUENCE DESCRIPTION: SEQ ID NO:12:

ACAGATTCGC GAACAGCTAT TAC                                               23

(2) INFORMATION FOR SEQ ID NO:13:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: Peptide Fragment (xi) SEQUENCE DESCRIPTION: SEQ ID NO:13:

Thr Asp Ser Arg Thr Ala Ile Tyr
    1               5

(2) INFORMATION FOR SEQ ID NO:14:

(i) SEQUENCE CHARACTERISTICS:
            (A) LENGTH: 33 base pairs
            (B) TYPE: nucleic acid
            (C) STRANDEDNESS: single

```
        ( D ) TOPOLOGY: linear ( i i ) MOLECULE TYPE: Oligonucleotide ( x i ) SEQUENCE DESCRIPTION: SEQ ID NO:14:

GGCTCCTTCA CAGATTCGCG AACAGCTATT TAC                                         33

( 2 ) INFORMATION FOR SEQ ID NO:15:

( i ) SEQUENCE CHARACTERISTICS:
            ( A ) LENGTH: 31 base pairs
            ( B ) TYPE: nucleic acid
            ( C ) STRANDEDNESS: single
            ( D ) TOPOLOGY: linear ( i i ) MOLECULE TYPE: Oligonucleotide ( x i ) SEQUENCE DESCRIPTION: SEQ ID NO:15:

CCCACGCGTA GGGACCGATG CCAAGATTCA G                                           31

( 2 ) INFORMATION FOR SEQ ID NO:16:

( i ) SEQUENCE CHARACTERISTICS:
            ( A ) LENGTH: 28 base pairs
            ( B ) TYPE: nucleic acid
            ( C ) STRANDEDNESS: single
            ( D ) TOPOLOGY: linear ( i i ) MOLECULE TYPE: Oligonucleotide ( x i ) SEQUENCE DESCRIPTION: SEQ ID NO:16:

CCCTCGCGAT GTGCTGGCGC TGGTGGTG                                               28
```

FIBRONECTIN PURIFICATION VECTOR

This invention was made with U.S. government support awarded by the National Institutes of Health (NIH) Grant No: HL 21644. The U.S. government has certain rights in this invention. This application is a continuation-in-part of 07/637,250, filed Jan. 3, 1991, U.S. Pat. No. 5,342,762.

TECHNICAL FIELD

This invention relates to uses of a vector to synthesize and efficiently purify proteins of interest. More particularly, it relates to modifying genetic material coding for the amino-terminal region of fibronectin and fusing DNA coding for proteins of interest to this region to help in the purification process.

BACKGROUND ART

Fibronectins are disulfide-bonded dimers found in vertebrates (e.g. mammals, birds, amphibians, fish, reptiles) that have been implicated in cell adhesion, wound healing, and embryogenesis. See E. Ruoslahti, 57 Ann. Rev. Biochem. 375–413 (1988); J. Thiery et al., in *Fibronectin*181–212 (Academic Press 1989); R. Colvin, in *Fibronectin*213–254 (Academic Press 1989); K. Yamada, in *Fibronectin*47–121 (Academic Press 1989).

The majority of fibronectin consists of three types of repeating homology units. T. Petersen, et al., 80 P.N.A.S. U.S.A. 137–141 (1983); T. Petersen et al., in *Fibronectin*163–179 (Academic Press 1989). Type I repeats contain two intrachain disulfide bonds and are present in the amino and carboxy-terminal regions of the molecule. Type II repeats are found only in a gelatin binding region of fibronectin and also contain two intrachain disulfide bonds. There are also 15–17 copies of type III repeats, which are located in the central portion of the molecule and lack intramolecular disulfide bonds.

Recent studies have shown that fibronectin becomes insolubilized into fibrils following binding to specific sites on the cell surface, termed matrix assembly sites. This binding is mediated by an amino-terminal 70 kDa fragment of fibronectin. The 70 kDa fragment contains nine copies of the type I repeat and two copies of the type II repeat. While much is known about the structure of fibronectins, the possibility of using all or part of a gene coding for the fibronectin gelatin binding region in a purification vector has not previously been suggested.

In connection with recombinant DNA technology it is often desirable to amplify large quantities of a vector (e.g. plasmid; phage), express proteinaceous material in a cell using the vector, cause the proteinaceous material to be secreted from the production cell into the surrounding media, and then purify the protein from the surrounding media. However, this process had not previously been optimized for expression of certain proteins. For example, while vectors had been created that efficiently express proteins, these proteins were often folded incorrectly, secreted inefficiently, or were difficult to separate from the surrounding media once secreted. These deficiencies caused reduced yield, impurities in the final product, and required the use of overly expensive and time consuming purification techniques.

A particularly desirable feature for techniques for expressing and purifying proteins via recombinant techniques is the ability to create a final product that does not contain extraneous fusion amino acids. This is especially critical in reducing regulatory delays in obtaining approval for use of such proteins.

SUMMARY OF THE INVENTION

In one embodiment, the present invention provides a method of isolating a selected protein. The method comprises a first step of obtaining a recombinant protein purification vector. The vector has a nucleotide sequence encoding a portion of fibronectin that binds to gelatin and a nucleotide sequence encoding the selected protein linked to the fibronectin encoding nucleotide sequence such that when the sequence encoding the selected protein is expressed, a fusion protein is produced. This fusion protein comprises the selected protein fused to the fibronectin portion. After the nucleotide sequence is expressed, the resulting fusion protein is exposed to a gelatin-containing affinity column. The fusion protein binds to the column. The fusion protein is then exposed to an endoprotease, wherein after the exposure the selected protein contains no more than one extraneous amino acid. An "extraneous amino acid" is defined as one that is not a part of the nucleotide sequence encoding the selected protein. This can then be exposed to a carboxypeptidase, wherein the extraneous amino acid is cleaved.

Preferably, the vector also has a leader nucleotide sequence coding for a signal peptide that assists in translocation of the fused product into the secretory apparatus of eukaryotic cells.

In another embodiment, the present invention is a protein produced by the claimed method.

We have designed a DNA expression vector such that DNA encoding a gelatin binding region of fibronectin can be expressed in a way so as to fuse it to foreign proteins of interest. The resulting fusion protein is designed so as to be secreted automatically from eukaryotic protein expression systems (e.g., insect cells, cos monkey cells). The fusion protein then binds strongly and substantially uniquely to a gelatin-containing affinity chromatography column, thereby yielding a highly purified product after elution. This fusion product can be digested with an endoprotease. A second pass through the column separates the fibronectin sequences from the protein. The protein of interest can then be eluted from the column.

Due to the design of the vector, the resulting protein will have no more than one extraneous amino acid. Where this is of concern, the system is designed so that treatment with a carboxypeptidase protease readily removes the extraneous amino acid.

Therefore, the objects of the present invention include providing methods as above which permit proteins to be efficiently produced and purified. A particularly important object is to be able to efficiently and quickly isolate proteins that do not have multiple extraneous amino acids. These and still other object and advantages of the present invention will be apparent from the description which follows.

The following embodiments do not represent the full scope of the invention. Rather, the invention may be employed in other embodiments. Reference is therefore to be made to the claims herein for interpreting the scope of the present invention.

BEST MODES FOR CARRYING OUT THE INVENTION

GE-1 Vector Overview

Figure 1:
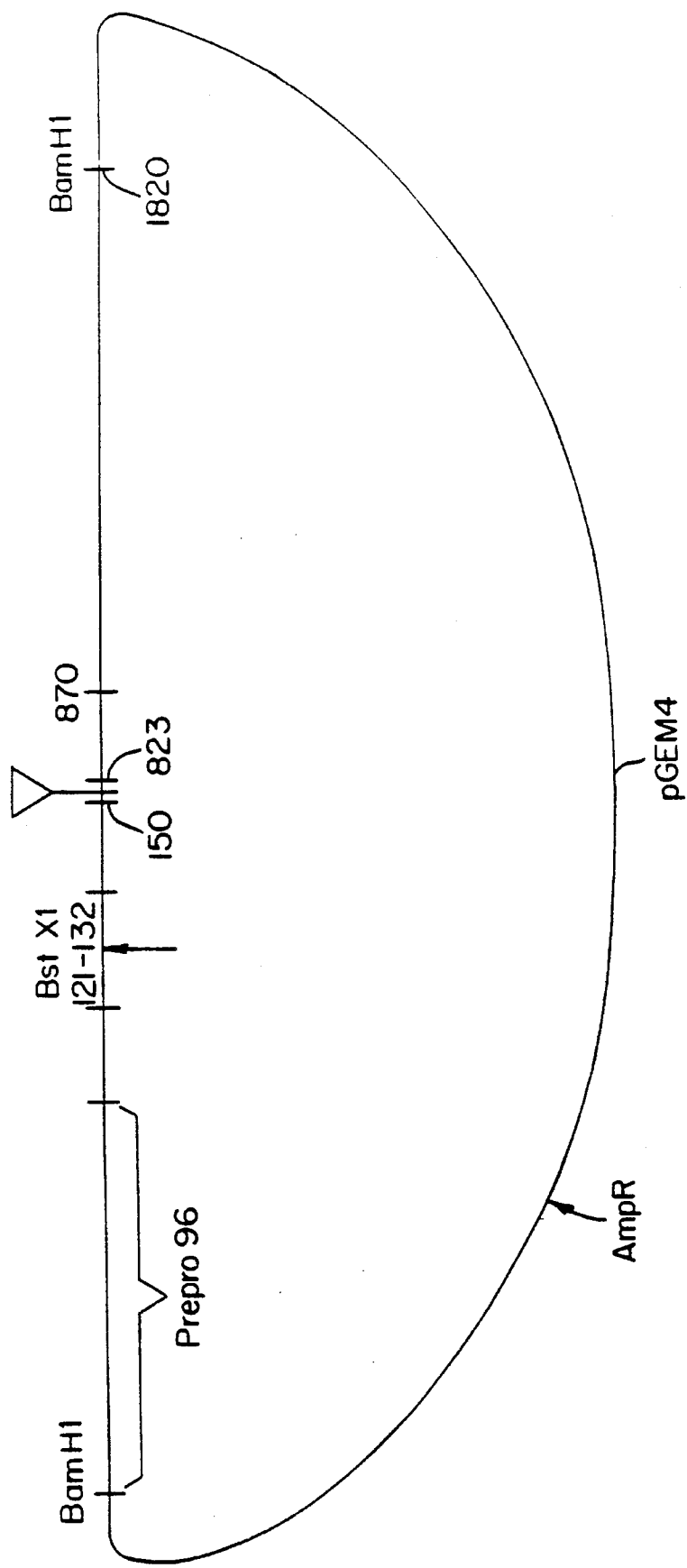
FIG. 1 schematically depicts the structure of the vector pGE-1/pGEM4.

Sections A–I describe the creation of the GE-1 vector and protein preparations using that vector.

A. Materials

BS70, a 1.8 kb 5' cDNA clone from rat fibronectin (S. Patel et al, 6 EMBO J. 2565–2572 (1987)) was obtained from J. Schwarzbauer (Princeton University, Princeton, N. J.). This clone is a HinfI-PstI fragment which contains 20 bp 5' to the ATG start codon and 1801 bp of coding sequence. This DNA (Fn571) encodes the first 571 amino acids of mature rat fibronectin, with a 5'32 amino acid preprosequence. BamHI linkers were added to the 5'end of the DNA, and an XbaI-SalI linker containing an in frame stop codon to the 3'end of the DNA. After the addition of BamHI linkers to the 3'end of this construct, the DNA was cloned into the BamHI linkers to the 3'end of this construct, the DNA was cloned into the BamHI cloning site of a standard baculovirus replacement vector, pAcYMI. See Y. Matsuura, et al., 67 J. Gen. Virol. 1515–1529 (1986). See also L. Miller, 42 *Ann. Rev. Microb.* 177–199 (1988).

The insect cell line IPLB-SF-21 (J. Vaughn et al., 13 In Vitro 213–217 (1977)) was a gift from P. Freisen (University of Wisconsin, Madison). SF-21 cells were cultured in TC100 medium (Gibco, Grand Island, N.Y.) containing 10% fetal calf serum (HyClone, Logan, Utah), supplemented with 0.6µg/ml amphotericin B (Gibco), 150 µg/ml Streptomycin-sulfate (Sigma, St. Louis, Mo.), and 99.7 U/ml penicillin (Sigma). Cells were grown to confluence (0.8–1.0 ×10$^6$ cells/ml) in monolayer culture at 27° C.

Nonrecombinant *Autographa californica* nuclear polyhedrosis virus (AcNPV) was a gift from P. Freisen. Viral DNA was prepared as described in D. Miller et al., 8 Genetic Engineering: Principles and methods 277–298 (1986).

Normal human fibroblast strain TJ6F was isolated in this laboratory. Cells were maintained in DME:F12 (1:1) (Gibco) containing 10% fetal calf serum. Normal rat kidney cells (NRK clone 495; American Tissue Type Collection, CRL 1570) were cultured in DME containing 10% calf serum.

B. Production Of The Recombinant Virus Fn571/AcNPV.

pAcYMI containing Fn571 cDNA was cotransfected with AcNPV DNA into SF-21 cells with lipofectin (BRL, Gaithersburg, Md.) according to manufacturer's instructions. Recombinant viruses were selected and plaque purified three times as described in D. Miller et al., 8 Genetic Engineering: Principles and Methods 277–298 (1986); M. Summers et al., Tex. Agric. Exp. Stn. Bull, 5–56 (1987). SF-21 cells (10$^7$ cells/100 mm dish) were infected with recombinant virus at a multiplicity of infection of 10–20 in serum containing medium. After 24 hours, the medium was removed, the cells were gently washed three times with serum free TC100, then incubated with 5 ml/dish serum free TC100 for 48 hours at 27° C. The conditioned medium was collected and centrifuged at 2500 rpm for ten minutes at room temperature. The supernatant was decanted and stored frozen until use.

C. Protein Purification.

Conditioned medium from Fn571 infected cells was applied to a gelatin-sepharose column (2 ml) at a flow rate of approximately 1 ml/min. The column was obtained by coupling gelatin to cyanogen bromide-activated agrose according to manufacture's instructions (Pharmacia). See also, F. Blumenstock et al., 132 Meth Enzym. 334–349 (1986) (gelatin sepharose). The column was washed with 0.15M NaCl, 20 mM Tris, pH 7.4 (Tris-buffered saline, TBS), then with 1M NaCl, 20 mM Tris, pH 7.4 prior to elution with 3M guanidine-HCl in TBS. The proteins were dialyzed against TBS, centrifuged to remove insoluble material, and stored at –135° C.

Conditioned medium isolated from Fn571/AcNPV infected cells was also analyzed by SDS PAGE for the presence of recombinant protein. This medium contained a 68 kDa protein which was absent from the medium of cells infected with an irrelevant recombinant virus. The recombinant protein was present at a concentration of approximately 15–25 µg/ml, and was the only protein which specifically bound to gelatin-sepharose.

Immunoblotting of conditioned medium from infected cells showed that the 68 kDa protein crossreacted with a polyclonal antibody to the 70 kDa fragment of human fibronectin. Medium from cells infected with an irrelevant recombinant virus did not contain any cross reacting proteins. This indicates that cells infected with Fn571/AcNPV produce a recombinant amino terminal fibronectin fragment.

The protein encoded by the Fn 571 construct is approximately 1–2 kDa smaller than the 70 kDa fragment produced by cathepsin digestion of human fibronectin. It should be noted in this regard that while rat fibronectin was used for the experiments described herein, gelatin binding regions of other vertebrate (e.g. mammalian) fibronectin DNA are also known. These should work in a similar manner.

D. Protease Digestion.

The r70 kDa protein (5µg) was digested with N-tosyl-L-phenylalanine choloromethyl ketone (TPCK)-trypsin (Cooper Biomedical, Malvern, Pa.) at a final concentration of 1 µg/ml for three minutes. Digestions were stopped by the addition of five fold excess of soybean trypsin inhibitor (Sigma). This cleaved the molecule between the fifth and sixth type I repeats. D. Mosher et al., 255 J. Biol. Chem. 1181–1188 (1980). Analysis of trypsin cleavage products showed that a 27 kDa peptide was generated and that the signal and presumptive pre-sequences had been cleaved from the r70 kDa protein. It should be appreciated that a variety of other proteases cleave at or near the trypsin site and can be substituted for trypsin.

E. Construction Of An Expression Vector.

Thus far we had used a baculovirus expression system to produce a r70 kDa protein from the amino terminal region of fibronectin. This protein was synthesized in large amounts, was secreted from the cells, and was easily purified from the medium of infected cells by binding to a gelatin containing column. In vitro mutagenesis, described below, was used to express a mutant protein lacking the first through third type I homology units. This protein was also secreted in large amounts and easily purified.

We then decided to try to replace most of the 27 kDa amino-terminal region with a domain from other extracellular proteins. Such hybrid proteins could then be purified by affinity chromatography on gelatin and later the domains isolated after proteolysis.

FN571 was cloned into the BamHI cloning site of M13 mp18 and used as a template for the first round of mutagenesis experiments. Oligonucleotide directed mutagenesis was performed according to T. Kunkel et al., in *Recombinant DNA Methodology* 587–601 (1989). Oligonucleotides were synthesized using an Applied Biosystems Automated DNA Synthesizer. An oligonucleotide designated GAP 1–3, TGGCTGTCAGTCAGAGCAAGGAGAAAT-GTTTTGATCACG (SEQ ID NO: 1), was used to delete the first through third type I homology units of fibronectin (bases 151–552; the A in the ATG start site is designated as 1). The fourth and fifth type I homology units (bases 553–882) were deleted from GAP1–3/M13 template DNA using the GAP 1–5 primer, GGTGGCTGTCAGTCAGAG-CAAGGTTCTACAGAGTCTTCAGC (SEQ ID NO: 2). The resulting GAP 1–5 phage was used to prepare single stranded DNA for the last round of mutagenesis. A 34-mer, CGTGCAGCCTCC<u>A</u>TCCCCGT<u>G</u>GGCTGTCAGTCAG (SEQ ID NO: 3), was designed to introduce a BstXI site (CCANNNNNNTGG, SEQ ID NO: 4) after position 128. Underlined bases represent substitutions of the wild type sequence.

In addition to creation of the BstXI site, the codon for Val-14 was changed to a tryptophan codon (numbering per Petersen et al., infra) with 1 being the first amino acid of the mature protein. Single-stranded DNA was sequenced through the AccI site at base 944 to confirm the mutations, and to verify that no other base changes were introduced. A 295 bp HindIII-AccI fragment from GE-1/M13 was then subcloned into FN571/pGEM72f that had been partially digested with HindIII/AccI to remove fibronectin sequences through the AccI site at base 944. pGEM72f was obtained from Promega. The resulting construct, GE-1/pGEM7Zf, contains a 672 bp deletion, and retains the intact coding region for the signal sequence, fact XIIIa site, trypsin site, and gelatin binding region of fibronectin.

Following digestion with BamHI, GE-1 was subcloned into pGEM4 (Promega, Madison, Wis.), which contains no BstX1 restriction enzyme site in the vector backbone, to yield pGE1/pGEM4. See FIG. 1. Plasmid pGE1/pGEM4 has been deposited at the American Type Culture Collection, Rockville, Md. U.S.A., in host DH5α cells, on Nov. 16, 1990 under the Budapest Treaty, with A.T.C.C. deposit #68480. This deposit (and the deposit of pGE2 referred hereafter) will be made available as required by applicable patent laws. Such availability is not to be construed as a license under any patent.

The pGEM4 backbone has amp resistance and a single BamHI site. It has no BstX1 site. GE1 begins at the 5' end with 96 nucleotides (32 amino acids) of fibronectin preprosequence which regulates secretion of the protein from the cell. This is a leader signal peptide that allows translocation of the fused protein.

There are then 54 nucleotides of mature fibronectin in which a BstX1 restriction site has been created at nucleotides 121–132. The 54 nucleotides code for a factor XIIIa cross linking site. See E. Barry et al., 263 *J. Biol. Chem.* 10464–69 (1988). Nucleotides 151–822 of fibronectin DNA have been deleted. Then follows fibronectin nucleotides 823–1808. Fibronectin nucleotides 823–1808 are disclosed at SEQ ID NO: 8. Nucleotide 1 of SEQ ID NO: 8 corresponds to nucleotide 823 in the fibronectin mRNA sequence. The trypsin cleavage site coding begins at nucleotide 870. The gelatin-binding region is coded for by nucleotides 3' of 870.

F. Insertion Of Genes In BstX1.

As an example of inserting a gene of interest in the BstX1 site, a gene coding for another part of fibronectin can be inserted in the purification vector. It will be appreciated that by similar techniques other DNA coding for proteins of interest can be expressed and purified. Eukaryotic genes (or parts of genes) coding for blood coagulation factor IX, the protease domain of factor IX, epidermal growth factor domains, thrombospondin, vitronectin, or kininogens are preferred, but numerous other genes (or parts of genes) may also be inserted. The term "foreign" in the claims therefore is intended to mean any non-fibronectin protein.

As an example, polymerase chain reaction (PCR) primers can be synthesized to amplify fibronectin cDNA encoding the 12th type I homology unit (I-12): primer A (antisense):

5'-GGCCACGGGGATGGGCCAGTGGTACCATCGGG-3', (SEQ ID NO: 5) primer B (sense): 5'-GGCCATCCCCGTGGGCAACGTGTTATGACGAC-3', (SEQ ID NO: 6). Underlined sequences represent bases introduced at the 5' ends of the fibronectin DNA to create a BstXI site for inframe cloning into GE-1/pGEM4.

PCR can be performed according to established procedures such as those of K. Mullis et al., 155 Meth. Enzym. 335–350 (1987), using Taq polymerase. A 3' fibronectin cDNA clone, BDP+7 (a gift from J. Schwarzbauer, Princeton University, Princeton, N. J. ) can be used as a template for amplification. Amplified DNA (198 bp) can be gel purified, digested with BstXI, then cloned into the BstXI cloning site of GE-1/pGEM4. Following digestion with BamHI, GE-1 can be subcloned into suitable expression cells such as the COS cell expression vector, pSVL (Pharmacia, Piscataway, N. J. ), the baculovirus expression vector, pAcYM1 (Y. Matsuura et al., 67 J. Gen. Virol. 1515–1529 (1986)), or BL1 (Invitrogen, San Diego, Calif.).

G. Expression Cells.

As an example, DNA can be transfected into COS-1 cells (a gift from D. Greenspan, University of Wisconsin, Madison) using DEAE-dextran (Pharmacia) as described in J. Sambrook et al., Molecular Cloning: A Laboratory Manual (2nd Ed. Cold Spring Harbor) 16.45–16.46 (1989). Cultures can be labelled with Tran $^{35}$S label (50 UCi/ml; ICN, Irvine, Calif.) 40–48 hours after transfection in serum free MEM lacking methionine and cysteine. Conditioned medium can be harvested after 20–24 hours, and applied to a 1 ml gelatin-agrarose column at a flow rate of 0.5 ml/minute. After washing sequentially with phosphate buffered saline (PBS) pH 7.4, 1M NaCl /10 mM tris, pH 7.4, and PBS, proteins can be eluted from the column with 3M guanidine-HCl in tris buffered saline (TBS), pH 7.4. Fractions (0.5 ml) can be counted on a scintillation counter, pooled, and dialyzed against TBS. The dialysate can be recovered, spun at 2500 rpm for ten minutes to remove insoluble materials, and recounted.

I-12/GE-1 can, in the alternative, be expressed in insect cells using a baculovirus expression system as described above. Conditioned medium can be harvested from infected cells and purified by a gelatin sepharose affinity chromatography, as described previously.

H. Trypsin Cleavage.

I-12 can be separated from the gelatin binding domain of fibronectin by mild digestion with 1 μg/ml trypsin for three minutes at room temperature as described above. The gelatin-binding 40 kDa fragment, as well as any undigested protein, can be separated from the I-12 protein by a second round of gelatin chromatography.

I. Other Protein Expressions Using the GE-1 Vector

The GE-1 vector has also successfully expressed non-fibronectin proteins (e.g. various parts of human Factor IX).

J. GE-2 Vector.

(a) In general.

It will be appreciated that the GE-1 vector described above leaves a "head" and a "tail" on the protein or protein domain of interest ("selected protein" ). That is, after cleavage and purification to remove the gelatin-binding part of fibronectin, fibronectin sequences remain. To achieve further benefits of the present invention, the GE-1 vector was modified to GE-2 so that the selected protein can be obtained with a minimum of extraneous sequence. Preferably, the selected protein has no extraneous sequences.

Figure 2:
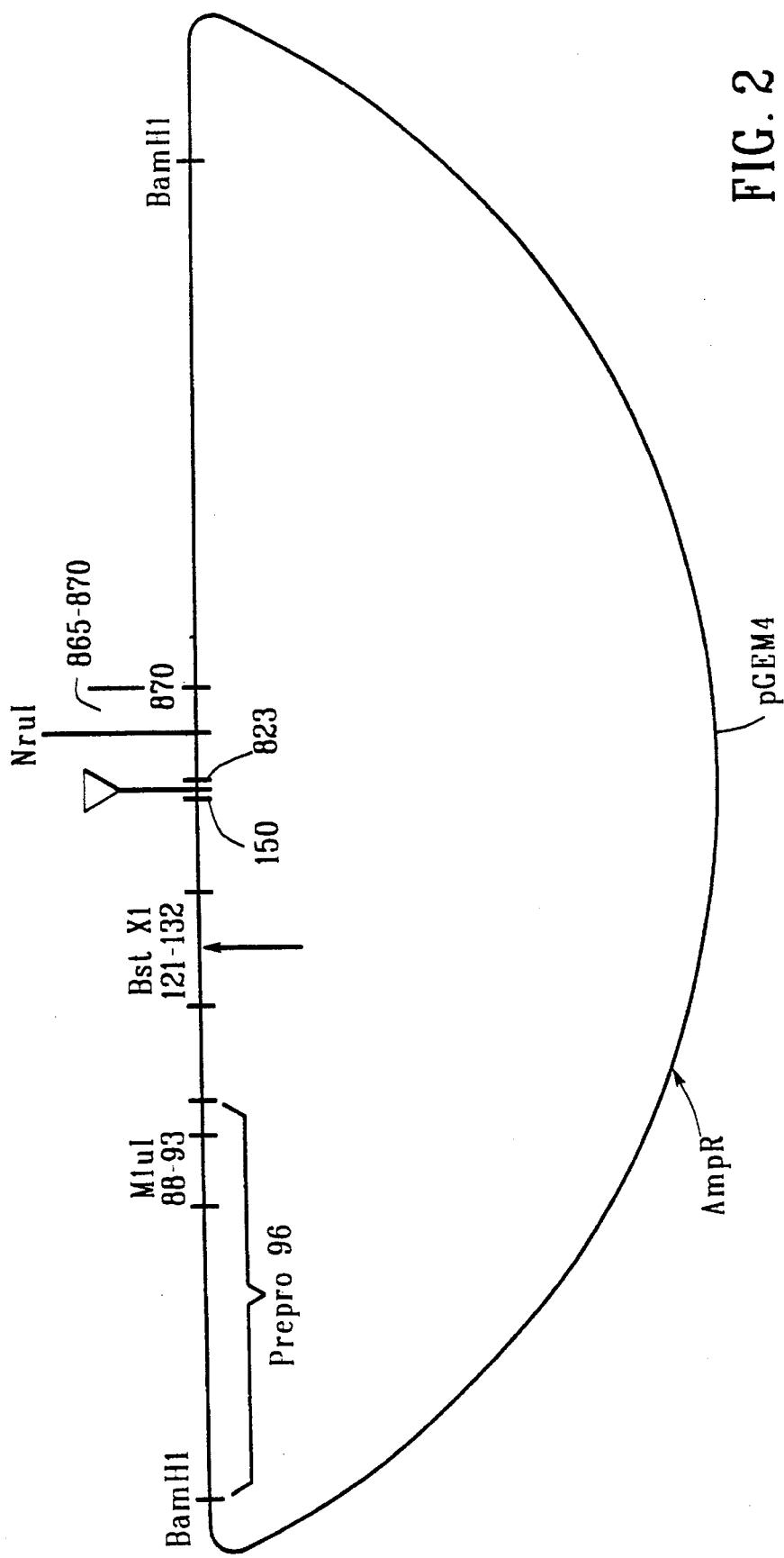
FIG. 2 schematically depicts the structure of the vector pGE-2/pGEM4.

The strategy involved introduction of cloning sites at two positions in the GE-1 vector: a MluI site in the sequence that directs intracellular proteolytic cleavage of profibronectin to yield mature fibronectin, and a NruI site in the sequence cleaved by trypsin-like proteases. A key difficulty we faced was to make these manipulations without adversely affecting the rest of the expressed proteins (e.g. intracellular proteolytic cleavage). FIG. 2 depicts GE-2 and the placement of the MluI and NruI sites.

After insertion of these two cleavage sites, a fibronectin fusion protein can be produced that will yield a selected protein with only one amino acid residue from fibronectin after cleavage with a protease, such as trypsin. The extraneous amino acid is a carboxyl-terminal Arg that can then be removed with carboxypeptidase B.

As described below, in the GE-2 vector the sequence of the propiece is changed from KSKR to KTRR. Introduction of the NruI site does not change any residues in the fibronectin-derived part of the fusion protein. NruI and MluI were also desirable because of all enzymes with 6-base recognition sequences, NruI and MluI are among those that cut the most rarely.

As described below, we have used GE-2 to successfully express tandem modules I-9 and III-1 of fibronectin in COS cells. Other coding sequences can be substituted for the modules we used.

(b) Removal of the extraneous head: Modification of bases 89–93 coding for the propeptide to generate a MluI site.

The sequence of GE-1 beginning at nucleotide 89 was changed to give the following twelve base pair sequence (SEQ ID NOs: 9 and 10):

```
amino acid:   K   T   R   R
nucleic acid: AAGACGCGTAGG
```

This was achieved as follows: An oligonucleotide GAAACCGGGAAGACGCGTAGGCAGGCTCAGC (SEQ ID NO: 11) was used to mutagenize GE-1 cloned into M13 to yield Mlu/GE-1. This mutagenesis was by standard molecular biological methods.

The underlined bases are changed from the GE-1 vector described above. The modified sequence is now an MluI site. The amino acid sequence of the fibronectin propiece is changed from KSKR to KTRR, but the S-to-T change is conservative and basic residues remain at positions −1, −2, and −4 to maintain the consensus sequence for processing proteases.

To insert a protein or domain of interest, one would preferably construct PCR primers with appropriate restriction site sequences at the ends and amplify the protein coding sequence of interest. In planning PCR primers, the "N-primer" should begin with the twelve base pair sequence (SEQ ID NO: 9) and continue with the first 6 or 7 codons of the protein to be expressed.

Cleavage of both GE-2 and the PCR product with MluI produces a 5'CGCG overhang to join the PCR product and GE-2. There are no other MluI sites in fibronectin or pGEM4.

(c) Removal of Most of the Extraneous Tail:

Modification of bases 865–867 coding for the −2 residue at the trypsin cleavage site to generate a NruI site.

The sequence of GE-1 beginning at nucleotide 865 was changed to give the sequence (SEQ ID NOs: 12 and 13):

```
amino acid:   T  D  S  R  T  A  I  Y
nucleic acid: ACAGATTCGCGAACAGCTATTTAC
```

This was achieved as follows: An oligonucleotide, GGCTCCTTCACAGATTCGCGAACAGCTATTTAC (SEQ ID NO: 14) was used to mutagenize GE-1 cloned into M13 to yield Nru/GE-1. This mutagenesis was by standard molecular biology techniques.

The underlined bases are changed from GE-1. The modified sequence now contains an NruI site.

Nru/GE-1 and Mlu/GE-1 DNA were sequenced to confirm the mutations, and subcloned (separately) into pGEM7Zf. After subcloning, the Mlu/GE-1/pGEM construct was digested with HindIII and BstXI to generate a 5'fragment from −22bp to 128bp (the HindIII site is in the multiple cloning region of pGEM). The Nru/GE-1/pGEM construct was digested with BstXI to generate a 999bp fragment. The HindIII-BstXI fragment from the MluI construct was ligated with the BstXI fragment from the NruI construct and with pGEM7Zf that was digested with HindIII and BstXI. The resulting construct, GE-2/pGEM7Zf, was sequenced to reconfirm the mutations and to check the sequences at the junction between the two fragments. GE-2 was then subcloned into pGEM4 and pSVL.

In planning the PCR primers for the protein sequence to be inserted, the "C-primer" should code for the last 7 or 8 codons of the protein to be expressed. The amplified fragment may be joined to NruI-cut GE-2 by blunt-end ligation. There are no NruI sites in fibronectin or pGEM4.

In GE-2, the remnants of fibronectin DNA left after removal of the type I modules act as a "stuffer" between the MluI and NruI sites and are removed when the PCR product containing the protein coding sequence is cloned into GE-2. The propiece ending in . . . KTRR is removed by a processing protease during secretion of the chimeric protein.

(d) Deposit

Plasmid pGE2/pGEM4 has been deposited at the American Type Culture Collection, Rockville, Md., U.S.A., in host DH5α cells, on Oct. 8, 1993, under the Budapest Treaty with A.T.C.C. deposit #69461.

(e) Cloning and purification of I-9 and III-1 .

Fibronectin modules I-9 and III-1 were amplified of rat fibronectin using the following two primers:

Primer A (antisense) (SEQ ID NO: 15):
5'CCCACGCGTAGGGACCGATGCCAAGATTCAG

Primer B (sense) (SEQ ID NO: 16):
5'CCCTCGCGATGTGCTGGCGCTGGTGGTG

The underlined sequences were added to the sequence of the fibronectin modules to introduce the MluI and NruI sites and, in the case of the antisense primer, to preserve the Arg at position -1. The product was digested with MluI and NrUI, and subcloned into GE-2/pGEM4. The insert was sequenced and then subcloned into pSVL. COS cells transfected with I-9-III-1/pSVL produced a protein of approximately 60 kDa reduced and higher mobility non-reduced when analyzed by SDS-PAGE after purifications on gelatin-Sepharose as described above.

(f) Cleavage of the Extraneous Residue.

After purification of the chimeric protein on gelatin-agarose and cleavage with trypsin, the only residue in the expressed protein remaining from fibronectin would be the R from the RTAIY sequence. One can then remove the R (Arg) with a carboxypeptidase, such as carboxypeptidase B (see Potts, J. T., In Meth. Enzymol. 11:644–664, 1967; Ambler, R. P., Meth. Enzymol.25:143–154, 1972.) By carboxypeptidase, we mean a peptidase capable of attacking the C-terminal end of a protein and removing one residue at a time. Thus, the final product should contain no extraneous residues.

K. Other Variants.

It should be appreciated that many other vectors can be designed with other unique ligation sites and the fibronectin gene. Also, while a gelatin-agarose or gelatin-Sepharose column is preferable, other affinity columns containing gelatin should also work.

While the protein can be expressed and purified bound to the gelatin binding region of fibronectin, it is preferred that after initially using the column that the gelatin binding region be cleaved off using trypsin or another protease.

A wide variety of fibronectin gelatin binding regions could be used with known amino terminal protease susceptibility. See *Fibronectin* p. 68–72, D. Mosher editor, (1989 Academic Press).

It should also be appreciated that the region around the BstX1 site (in GE-1) after cleavage codes for an amino acid sequence beginning:

pEAQQIVQPPSpWxxx . . . xxxPSPWAVSQSKVLQ SASAGSGSFTDVR . . .

(SEQ ID NO: 7) where pE-pyroglutamic acid (first amino acid of the mature protein), Q=target for modification by factor XIIIa, W=change from the wild type sequence, xxx . . .xxx=the sequence of the inserted foreign amino acids, PSPW=an extra sequence introduced by the 3'half of the BstXI site, KV=junction between gapped out natural sequences, S=residues that can be mutated to C and become targets for modification with cysteine-specific reagents if desired, and R=new carboxyl terminal after trypsinization.

Industrial Applicability

The present invention provides a means to efficiently produce and purify large quantities of a desired protein without any exogenous structure.

---

We claim:

1. A method of isolating a selected foreign protein comprising the steps of:
   (a) obtaining a eukaryotic expression vector which comprises a first nucleotide sequence encoding a portion of fibronectin that binds to gelatin, wherein the nucleotide sequence is also present in nucleotides 823–1808 of the fibronectin gene of SEQ ID NO:8, and a second nucleotide sequence encoding the selected foreign protein, said second sequence being linked immediately 5' to the first sequence such that when the second sequence is expressed, a fusion protein which is the selected protein fused immediately upstream to the fibronectin portion is produced;
   (b) expressing the first and second sequence in a eukaryotic host cell, wherein a fusion protein is formed;
   (c) exposing the fusion protein of step (b) to a gelatin-containing affinity column, wherein the fusion protein binds to the column; and
   (d) exposing the fusion protein to an endoprotease, wherein after the exposure the selected foreign protein contains no more than one extraneous amino acid.

2. The method of claim 1 wherein the product of step (d) has an extraneous amino acid and wherein the method additionally comprises the step of treating the product of step (d) with a carboxypeptidase capable of removing the extraneous amino acid.

3. The method of claim 2, wherein the carboxypeptidase is carboxypeptidase B.

4. (Amended) The method of claim 1, wherein the vector also contains a leader nucleotide sequence 5' to the second sequence.

5. The method of claim 1, wherein the endoprotease is trypsin.

* * * * *